United States Patent
Ishikawa (10) Patent No.: US 10,492,689 B2
(45) Date of Patent: Dec. 3, 2019

(54) OPTICAL MEASUREMENT SYSTEM AND OPTICAL MEASUREMENT APPARATUS

(71) Applicant: Shimadzu Corporation, Kyoto-shi (JP)

(72) Inventor: Akihiro Ishikawa, Kyoto (JP)

(73) Assignee: Shimadzu Corporation, Nishinokyo-Kuwabaracho, Nakagyo-ku, Kyoto-shi, Kyoto (JP)

(*) Notice: Subject to any disclaimer, the term of this patent is extended or adjusted under 35 U.S.C. 154(b) by 420 days.

(21) Appl. No.: 14/749,464

(22) Filed: Jun. 24, 2015

(65) Prior Publication Data
US 2016/0374558 A1    Dec. 29, 2016

(51) Int. Cl.
*A61B 5/00*    (2006.01)
*A61B 5/1455*  (2006.01)

(52) U.S. Cl.
CPC .......... *A61B 5/0059* (2013.01); *A61B 5/1455* (2013.01); *A61B 5/4064* (2013.01)

(58) Field of Classification Search
CPC .... A61B 5/0059; A61B 5/4064; A61B 5/1455
See application file for complete search history.

(56) References Cited

U.S. PATENT DOCUMENTS

| | | | |
|---|---|---|---|
| 2012/0238883 A1* | 9/2012 | Inoue | A61B 5/0059 600/476 |
| 2013/0102907 A1* | 4/2013 | Funane | A61B 5/0075 600/476 |
| 2013/0300829 A1* | 11/2013 | Urasaki | A61B 1/00009 348/45 |

FOREIGN PATENT DOCUMENTS

| | | |
|---|---|---|
| JP | 2005-349027 A | 12/2005 |
| JP | 2008-173140 A | 7/2008 |

* cited by examiner

*Primary Examiner* — Rochelle D Turchen
(74) *Attorney, Agent, or Firm* — Muir Patent Law, PLLC (57) ABSTRACT

An optical measurement system includes a portable type optical measurement apparatus and a non-portable type optical measurement apparatus larger than the portable optical measurement apparatus. The non-portable type optical measurement apparatus is configured to be communicable to the portable type optical measurement apparatus and to be operated as a main measurement apparatus which executes measurement condition settings and measurement controls based on an input operation from the operation input section and also executes measurement condition settings and measurement controls of the non-portable type optical measurement apparatus by communication. The portable type measurement apparatus is capable of measuring a subject independently of the non-portable type measurement apparatus, and is operated as a sub-measuring apparatus for executing measurement condition settings and measurement controls in accordance with a control by the non-portable type measurement apparatus.

8 Claims, 4 Drawing Sheets

Fig. 4

OPTICAL MEASUREMENT SYSTEM AND OPTICAL MEASUREMENT APPARATUS

BACKGROUND

The present disclosure relates to an optical measurement system and an optical measurement apparatus, and more specifically to an optical measurement system and an optical measurement apparatus in which a measurement is performed by irradiating a measurement light onto a subject and receiving the measurement light emitted outside from the subject.

Conventionally, an optical measurement apparatus is known in which a measurement is performed by irradiating a measurement light onto a subject and receiving the measurement light emitted outside from the subject (see, e.g., Patent Documents 1 and 2, each of which is incorporated herein by reference in its entirety).

In the aforementioned Patent Document 1, an optical measurement apparatus is disclosed, in which a measurement light is output from a measurement apparatus main body via an optical fiber cable to a light transmitting probe mounted on a head of a subject and the measurement light reflected (scattered) in a brain is received by a light receiving probe via an optical cable to be detected. This optical measurement apparatus is a carriage-type apparatus having wheels, which is a transportable (conveyable) type apparatus capable of approaching close to a subject for a measurement.

In the aforementioned Patent Document 2, an optical measurement apparatus (portable type) is disclosed, in which it is configured such that a measuring equipment in which plural light sources and plural detectors are arranged is mounted on a head in a portable manner. Light sources and detectors are connected to a measuring apparatus by cables, and the control of the light sources and detectors is performed on the measuring apparatus side.

Such optical measurement apparatus is used as a means for non-invasively measuring a brain function of a human body by obtaining a bloodstream distribution of a brain of a subject from optical measurement results, and especially used in research institutions, medical institutions, etc., related to brain science. The conveyable type as disclosed in the aforementioned Patent Document 1 is high in restriction to a subject, and therefore a measurement is performed mostly in a state not accompanying the subject's movements. Further, in the portable type as disclosed by the aforementioned Patent Document 2, the measuring equipment can be mounted on a subject, and therefore, for example, a measurement can be performed in a state closed to a daily performance, but an external computer is typically required to perform settings of measuring conditions for a measuring apparatus or processing and management of measured data. For this reason, the conveyable type apparatus and the portable type apparatus were conventionally used depending on the intended purpose or the usage environment (utilization purpose) as a separate independent apparatus.

[Patent Document 1] Japanese Unexamined Patent Application Publication No. 2005-349027.

[Patent Document 2] Japanese Unexamined Patent Application Publication No. 2008-173140.

Since an optical measurement apparatus is used in an academic field of brain science, there is a demand to perform various measuring methods in various environments depending on research contents. In order to meet this demand, it is desirable to prepare both of the conveyable type and the portable type so that both types can be selectively used depending on the application (research contents). However, in cases where there is a need to increase the number of measurement channels, such as, e.g., a case in which there is a demand to obtain more detail data or a case in which there is a demand to simultaneously perform measurements of a plurality of subjects, it is likely to be necessary to prepare an optical measurement apparatus which is the same type of an optical measurement apparatus (conveyable type or portable type). This requires a possession of plural apparatuses on each of both types, which increases additional capital investments. Further, for a portable type apparatus, it is likely necessary to prepare an external computer. Also from this view point, an additional capital investment increases. Therefore, conventionally, it is difficult to cope with the usage in various applications and/or usage environments while suppressing additional capital investments.

The description herein of advantages and disadvantages of various features, embodiments, methods, and apparatus disclosed in other publications is in no way intended to limit the present invention. For example, certain features of the described embodiments of the invention may be capable of overcoming certain disadvantages and/or providing certain advantages, such as, e.g., disadvantages and/or advantages discussed herein, while retaining some or all of the features, embodiments, methods, and apparatus disclosed therein.

SUMMARY

The disclosed embodiments of the present invention have been developed in view of the above-mentioned and/or other problems in the related art. The disclosed embodiments of the present invention can significantly improve upon existing methods and/or apparatuses.

One aspect of the present disclosure describes an optical measurement system and an optical measurement apparatus capable of being utilized for various applications and/or in various usage environments while suppressing an additional capital investment when using optical measurement apparatuses of both types of apparatus, i.e., a portable type measurement apparatus and a non-portable type measurement apparatus.

An optical measurement system according to a first aspect of the present invention includes a portable type measurement apparatus configured to measure a subject by irradiating a measurement light from a first light transmitting terminal to the subject and receiving the measurement light emitted outside from the subject by a first light receiving terminal, and a non-portable type measurement apparatus larger than the portable type measurement apparatus, the non-portable type measurement apparatus being configured to be able to measure the subject independently of the portable type measurement apparatus by irradiating a measurement light from a second light transmitting terminal to the subject and receiving the measurement light emitted outside from the subject by a second light receiving terminal. The non-portable type measurement apparatus is configured to be communicable to the portable type measurement apparatus and to be operated as a main measurement apparatus, which executes measurement condition settings and measurement controls based on an input operation from the operation input section and also executes measurement condition settings and measurement controls of the portable type measurement apparatus by communication. The portable type measurement apparatus is configured to be able to measure the subject independently of the non-portable type measurement apparatus and to be operated as a sub-measurement apparatus which executes measurement condition settings and measurement controls based on a control of the non-portable type measurement apparatus.

In the optical measurement system according to the first aspect of the present invention, as mentioned above, the non-portable type measurement apparatus is configured to be communicable to the portable type measurement apparatus and to be operated as a main measurement apparatus which executes measurement condition settings and measurement controls based on an input operation from the operation input section and also executes measurement condition settings and measurement controls of the portable type measurement apparatus by communication, and the portable type measurement apparatus is configured to be able to measure the subject independently of the non-portable type measurement apparatus and to be operated as a sub-measurement apparatus which executes measurement condition settings and measurement controls based on a control of the non-portable type measurement apparatus. Therefore, the portable type measurement apparatus is regarded as a slave apparatus, and the larger non-portable-portable type measurement apparatus is regarded as a master apparatus. Thus, measurement condition settings and measurement controls of the portable type measurement apparatus can be executed on the non-portable-portable type measurement apparatus side. As a result, if there are a portable type measurement apparatus and a non-portable type measurement apparatus, it becomes possible not only to separately use respective apparatus depending on the intended-purpose, but also to increase the measurement channel number by operating the portable type measurement apparatus and the non-portable type measurement apparatus in coordination with each other, or to measure a plurality of subjects by the portable type measurement apparatus and the non-portable type measurement apparatus with sharing the burden. Further, since measurement condition settings and measurement controls of the portable type measurement apparatus can be performed using the operation input section of the non-portable type measurement apparatus, it is not required to prepare an external computer which was conventionally required for a portable type apparatus. As a result, in the case of utilizing both types of optical measurement apparatuses, i.e., a portable type optical measurement apparatus and a conveyable type optical measurement apparatus, it becomes possible to obtain an optical measurement system capable of being utilized for various purposes or in various usage environments while restraining additional capital investments.

In the optical measurement system according to the aforementioned first aspect, the non-portable type measurement apparatus may be configured to be able to control the portable type measurement apparatus so as to execute a measurement operation of the non-portable type measurement apparatus and a measurement operation of the portable type measurement apparatus in synchronization. With this, for example, by using both the non-portable type optical measurement apparatus and the portable type optical measurement apparatus together, synchronous measurements for one or a plurality of subjects can be performed simultaneously.

In the optical measurement system according to the aforementioned first aspect, the non-portable type measurement apparatus may further include a main storage part for storing measured data, and may be configured to be able to obtain measured data of the portable type measurement apparatus by communication and store the obtained measured data in the main storage part. With this, since the measured data obtained by the portable type measurement apparatus can be administered on the non-portable type optical measurement apparatus side, it is not required to prepare an external computer and additional capital investment can be restrained. Further, both the measured data of the non-portable type measurement apparatus and the portable type measurement apparatus can be stored in the main storage part of the non-portable type measurement apparatus. Therefore, in the case of operating the non-portable type measurement apparatus and the portable type measurement apparatus together, measured data comparison and/or integration can be easily performed without requiring any measured data transferring operations between the apparatuses.

In this case, in cases where the non-portable type measurement apparatus and the portable type measurement apparatus respectively perform a measurement operation for a plurality of subjects, the non-portable type measurement apparatus is configured such that the measurement operation of the non-portable type measurement apparatus for one subject and the measurement operation of the portable type measurement apparatus for another subject are synchronized and the measured data of the non-portable type measurement apparatus and the measured data of the portable type measurement apparatus are stored in the main storage part separately. With this structure, without preparing a plurality of same apparatuses, a plurality of subjects can be measured in synchronization. Also in this case, without requiring measured data transferring operations between apparatuses, a comparison between data, etc., can be performed only by the existing non-portable type measurement apparatus.

In the structure in which the aforementioned non-portable type measurement apparatus includes the main storage part, for example, in cases where the non-portable type measurement apparatus and the portable type measurement apparatus perform a measurement operation for a same subject, the non-portable type measurement apparatus is configured such that the measurement operation of the non-portable type measurement apparatus and the measurement operation of the portable type measurement apparatus are synchronized and the measured data of the non-portable type measurement apparatus and the measured data of the portable type measurement apparatus are integrally stored in the main storage part. With this structure, without preparing a plurality of same apparatuses, measurements can be performed only by the existing apparatuses (portable type measurement apparatus and non-portable type measurement apparatus) with an increased measurable channel numbers. Further, without requiring the measured data transferring operations between apparatuses, both the measured data of the non-portable type measurement apparatus and the portable type measurement apparatus can be managed as single measured data by integrating the measured data of the non-portable type measurement apparatus and the portable type measurement apparatus on the non-portable type measurement apparatus side.

In the structure in which the aforementioned non-portable type measurement apparatus includes the main storage part, for example, in cases where a measurement of the subject is performed only by the portable type measurement apparatus, the non-portable type measurement apparatus is configured to control the measurement operation of the portable type measurement apparatus, obtains the measured data of the portable type measurement apparatus and stores the obtained measured data of the portable type measurement apparatus in the main storage part independently of the measured data of the non-portable type measurement apparatus. With this structure, even in the case of using the portable type measurement apparatus alone, an external computer which was conventionally required when a portable type was used can be eliminated. For this reason, while restraining additional capital investments, various applications can be dealt only by the existing non-portable type measurement apparatus and the portable type measurement apparatus.

In the optical measurement system according to the first aspect, for example, the portable type measurement apparatus may include a first light output part for outputting the measurement light to a first light transmitting terminal, a first light detection part for detecting the measurement light received from a first light receiving terminal, a first communication part, and a first control part for performing a measurement operation control, and the non-portable type measurement apparatus includes a second light output part for outputting the measurement light to the second light transmitting terminal, a second light detection part for detecting the measurement light received from the second light receiving terminal, a second communication part communicable to the first communication part of the portable type measurement apparatus, a second control part performing a measurement operation control, a display section, and the operation input section. With this structure, it becomes possible to structure a portable type measurement apparatus and a non-portable type measurement apparatus independently measurable and communicable with each other. Further, by providing the display section and the operation input section to the non-portable type measurement apparatus, without preparing an external display device, etc., operations for the measurement condition setting of the portable type measurement apparatus can be performed only by the non-portable type measurement apparatus.

The optical measurement apparatus according to a second aspect of the present invention includes a portable type measurement apparatus including a first light output part for outputting a measurement light to a first light transmitting terminal, a first light detection part for detecting the measurement light received from a first light receiving terminal, a first communication part, and a first control part for performing a measurement operation control, and a non-portable type measurement apparatus larger than the portable type measurement apparatus, including a second light output part for outputting the measurement light to the second light transmitting terminal, a second light detection part for detecting the measurement light received from the second light receiving terminal, a second communication part communicable to the first communication part of the portable type measurement apparatus, a second control part for performing a measurement operation control, and an operation input section for receiving an input operation. The portable type measurement apparatus and the non-portable type measurement apparatus are configured so as to be able to independently measure the subject by receiving the measurement light irradiated from the first light transmitting terminal and the second light transmitting terminal to the subject and emitted outside from the subject. The second control part of the non-portable type measurement apparatus is configured to be operated as a main measurement apparatus which executes measurement condition settings and measurement controls of the non-portable type measurement apparatus based on an input operation from the operation input section and also executes measurement condition settings and measurement controls of the portable type measurement apparatus by communication. The first control part of the portable type measurement apparatus is configured to be operated as a sub-measurement apparatus which executes measurement condition settings and measurement controls of the portable type measurement apparatus based on a control by the second control part.

In the optical measurement system according to the second aspect of the present invention, as explained above, the second control part of the non-portable type measurement apparatus is configured to make the second control part of the non-portable type measurement apparatus execute the measurement condition settings and measurement controls of the non-portable type measurement apparatus based on the input operation from the operation input section and operate as a main control part for executing measurement condition settings and measurement controls of the portable type measurement apparatus by communication and also configured to operate as a sub control part for executing measurement condition settings and measurement controls of the portable type measurement apparatus in accordance with a control by making the first control part of the portable type measurement apparatus operate as a main control part for executing the measurement condition settings and the measurement controls based on an input operation of the operation input section and executing the measurement condition setting and the measurement controls of the portable type measurement apparatus in accordance with the control by the second control part. The portable type measurement apparatus is regarded as a slave apparatus, and the larger non-portable type measurement apparatus is regarded as a master apparatus. Thus, measurement condition settings and measurement controls of the portable type measurement apparatus can be executed on the non-portable type measurement apparatus side. As a result, if there are a portable type measurement apparatus and a non-portable type measurement apparatus, it becomes possible not only to separately use respective apparatuses depending on the intended-purpose, but also to increase the measurement channel number by operating the portable measurement apparatus and the non-portable measurement apparatus in coordination with each other, or to measure a plurality of subjects by the portable type measurement apparatus and the non-portable type measurement apparatus with sharing the burden. Further, since measurement condition settings and measurement controls of the portable type measurement apparatus can be performed using the operation input section of the non-portable measurement apparatus, it is not required to prepare an external computer which was conventionally required for a portable type apparatus. As a result, in the case of utilizing both types of optical measurement apparatuses, i.e., a portable type optical measurement apparatus and a conveyable type optical measurement apparatus, it becomes possible to obtain an optical measurement system capable of being utilized for various purposes or in various usage environments while restraining additional capital investments. As a result, in the case of utilizing both types of optical measurement apparatuses, i.e., a portable type optical measurement apparatus and a conveyable type optical measurement apparatus, it becomes possible to obtain an optical measurement system capable of being utilized for various purposes or in various usage environments while restraining additional capital investments. The optical measurement apparatus according to a third aspect of the present invention is formed to be larger than a portable type measurement apparatus including a first light output part for outputting a measurement light to a first light transmitting terminal, a first light detection part for detecting the measurement light received from a first light receiving terminal, a first communication part, and a first control part for performing a measurement operation control, the portable type measurement apparatus being configured to perform a measurement operation of the subject by receiving the measurement light emitted outside from the subject. The optical measurement apparatus includes a second light output part configured to output the measurement light to a second light transmitting terminal, a second light detection part configured to detect the measurement light received from a second light receiving terminal, a second communication part communicable to the first communication part of the portable type measurement apparatus, a second control part configured to perform a measurement operation control, and an operation input section configured to receive an input operation. It is configured to perform a measurement operation of the subject independently of the portable type measurement apparatus by receiving the measurement light irradiated from the second light transmitting terminal to the subject and emitted outside from the subject. The second control part is configured to make the first control part of the portable type measurement apparatus operate as a sub control part for executing measurement condition settings and measurement controls of the portable type measurement apparatus in accordance with a control by operating as a main control part for executing the measurement condition settings and the measurement controls based on an input operation of the operation input section and executing the measurement condition setting and the measurement controls of the portable type measurement apparatus by communication.

In the optical measurement system according to the third aspect of the present invention, as mentioned above, the second control part is configured to be operated as a main measurement apparatus which executes measurement condition settings and measurement controls of the non-portable measurement apparatus based on an input operation from the operation input section and also executes measurement condition settings and measurement controls of the portable measurement apparatus by communication. The first control part of the portable type measurement apparatus is configured to be operated as a sub-controls section for executing measurement condition settings and measurement controls of the portable type measurement apparatus based on a control by the second control part. Therefore, the portable type measurement apparatus can be regarded as a slave apparatus, and the larger non-portable type measurement apparatus can be regarded as a master apparatus. Thus, measurement condition settings and measurement controls of the portable type measurement apparatus can be executed on the non-portable type measurement apparatus side. As a result, if there are a portable type measurement apparatus and a non-portable type measurement apparatus, it becomes possible not only to separately use respective apparatuses depending on the intended-purpose, but also to increase the measurement channel number by operating the portable measurement apparatus and the non-portable measurement apparatus in coordination with each other, or to measure a plurality of subjects by the portable type measurement apparatus and the non-portable type measurement apparatus with sharing the burden. Further, since measurement condition settings and measurement controls of the portable type measurement apparatus can be performed using the operation input section of the non-portable measurement apparatus, it is not required to prepare an external computer which was conventionally required for a portable type apparatus. As a result, in the case of utilizing both types of optical measurement apparatuses, i.e., a portable type optical measurement apparatus and a conveyable type optical measurement apparatus, it becomes possible to obtain an optical measurement system capable of being utilized for various purposes or in various usage environments while restraining additional capital investments.

According to certain aspects of the present invention, in the case of utilizing both types of optical measurement apparatuses, e.g., a portable type optical measurement apparatus and a conveyable type optical measurement apparatus, it becomes possible to obtain an optical measurement system capable of being utilized for various purposes or in various usage environments while restraining additional capital investments.

The above and/or other aspects, features and/or advantages of various embodiments will be further appreciated in view of the following description in conjunction with the accompanying figures. Various embodiments can include and/or exclude different aspects, features and/or advantages where applicable. In addition, various embodiments can combine one or more aspect or feature of other embodiments where applicable. The descriptions of aspects, features and/or advantages of particular embodiments should not be construed as limiting other embodiments or the claims. In the drawings, the size and relative sizes of layers and regions may be exaggerated for clarity. Like numbers refer to like elements throughout. The terminology used herein is for the purpose of describing particular embodiments only and is not intended to be limiting of the invention. As used herein, the singular forms "a", "an" and "the" are intended to include the plural forms as well, unless the context clearly indicates otherwise. As used herein, the term "and/or" includes any and all combinations of one or more of the associated listed items and may be abbreviated as "/". It will be understood that, although the terms first, second, etc. may be used herein to describe various elements, these elements should not be limited by these terms. Unless indicated otherwise, these terms are only used to distinguish one element from another. For example, a first object could be termed a second object, and, similarly, a second object could be termed a first object without departing from the teachings of the disclosure. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof. It will be understood that when an element is referred to as being "connected" or "coupled" to or "on" another element, it can be directly connected or coupled to or on the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.). However, the term "contact," as used herein refers to direct contact (i.e., touching) unless the context indicates otherwise. Terms such as "same," "planar," or "coplanar," as used herein when referring to orientation, layout, location, shapes, sizes, amounts, or other measures do not necessarily mean an exactly identical orientation, layout, location, shape, size, amount, or other measure, but are intended to encompass nearly identical orientation, layout, location, shapes, sizes, amounts, or other measures within acceptable variations that may occur, for example, due to manufacturing processes. The term "substantially" may be used herein to reflect this meaning. Unless otherwise defined, all terms (including technical and scientific terms)

used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and/or the present application, and will not be interpreted in an idealized or overly formal sense unless expressly so defined herein.

BRIEF DESCRIPTION OF THE DRAWINGS

The disclosed embodiments of the present invention are shown by way of example, and not limitation, in the accompanying figures.

DETAILED DESCRIPTION

In the following paragraphs, some embodiments of the invention will be described by way of example and not limitation. It should be understood based on this disclosure that various other modifications can be made by those in the art based on these illustrated embodiments.

Hereinafter, various embodiments of the present invention will be explained with reference to on the attached drawings.

Though various embodiments are described herein, the invention may, be embodied in many different forms and should not be construed as limited to the example embodiments set forth herein. These example embodiments are just that—examples—and many implementations and variations are possible that do not require the details provided herein. It should also be emphasized that the disclosure provides details of alternative examples, but such listing of alternatives is not exhaustive. Furthermore, any consistency of detail between various examples should not be interpreted as requiring such detail—it is impracticable to list every possible variation for every feature described herein. The language of the claims should be referenced in determining the requirements of the invention.

In the drawings, the size and relative sizes of layers and regions may be exaggerated for clarity. Like numbers refer to like elements throughout.

As used herein, the singular forms "a", "an" and "the" are intended to include the plural forms as well, unless the context clearly indicates otherwise. As used herein, the term "and/or" includes any and all combinations of one or more of the associated listed items and may be abbreviated as "/".

It will be understood that, although the terms first, second, third etc. may be used herein to describe various elements, components, or steps, these elements, components, and steps should not be limited by these terms. Unless the context indicates otherwise, these terms are only used to distinguish one element, component, of step from another element, component, or step, for example as a naming convention. Thus, a first element, component, or step discussed below in one section of the specification could be termed a second element, component, or step in another section of the specification or in the claims without departing from the teachings of the present disclosure. In addition, in certain cases, even if a term is not described using "first," "second," etc., in the specification, it may still be referred to as "first" or "second" in a claim in order to distinguish different claimed elements from each other.

It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

It will be understood that when an element is referred to as being "connected" or "coupled" to or "on" another element, it can be directly connected or coupled to or on the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

Relative terms, such as "beneath," "below," "lower," "above," "upper" and the like, may be used herein for ease of description to describe one element's or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" can encompass both an orientation of above and below. The device may be otherwise oriented (rotated 90 degrees or at other orientations) and the spatially relative descriptors used herein interpreted accordingly.

Terms such as "same," "planar," or "coplanar," as used herein when referring to orientation, layout, location, shapes, sizes, amounts, or other measures do not necessarily mean an exactly identical orientation, layout, location, shape, size, amount, or other measure, but are intended to encompass nearly identical orientation, layout, location, shapes, sizes, amounts, or other measures within acceptable variations that may occur, for example, due to manufacturing processes. The term "substantially" may be used herein to reflect this meaning.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and/or the present application, and will not be interpreted in an idealized or overly formal sense unless expressly so defined herein.

Initially, referring to FIGS. 1 to 3, an entire structure of an optical measurement system 100 according to one embodiment of the present invention will be explained. In this embodiment, as one example of an optical measurement system, the following explanation will be directed to an optical measurement system 100 constituted by two optical measurement apparatuses including one conveyable type optical measurement apparatus 1 and one portable type optical measurement apparatus 2. The optical measurement apparatus 1 is one example of a "non-portable type measurement apparatus" of the present invention. Further, the optical measurement apparatus 2 is one example of a "portable type measurement apparatus" of the present invention.

Figure 1:
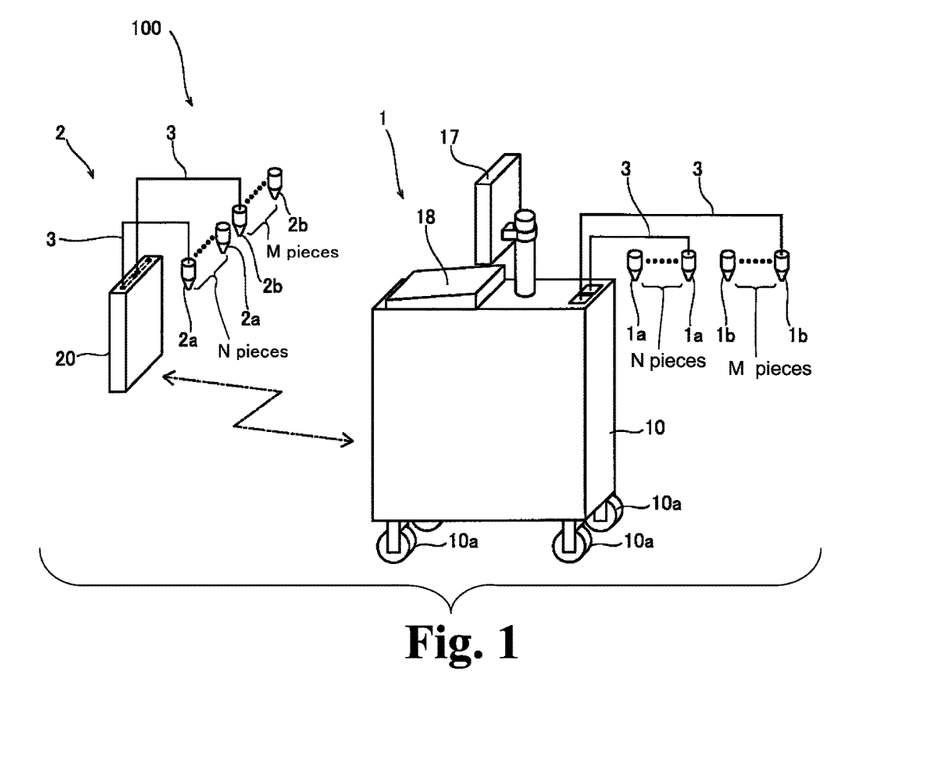
FIG. 1 is a schematic drawing showing an entire structure of an optical measurement system according to certain embodiments of the present invention.
Figure 2:
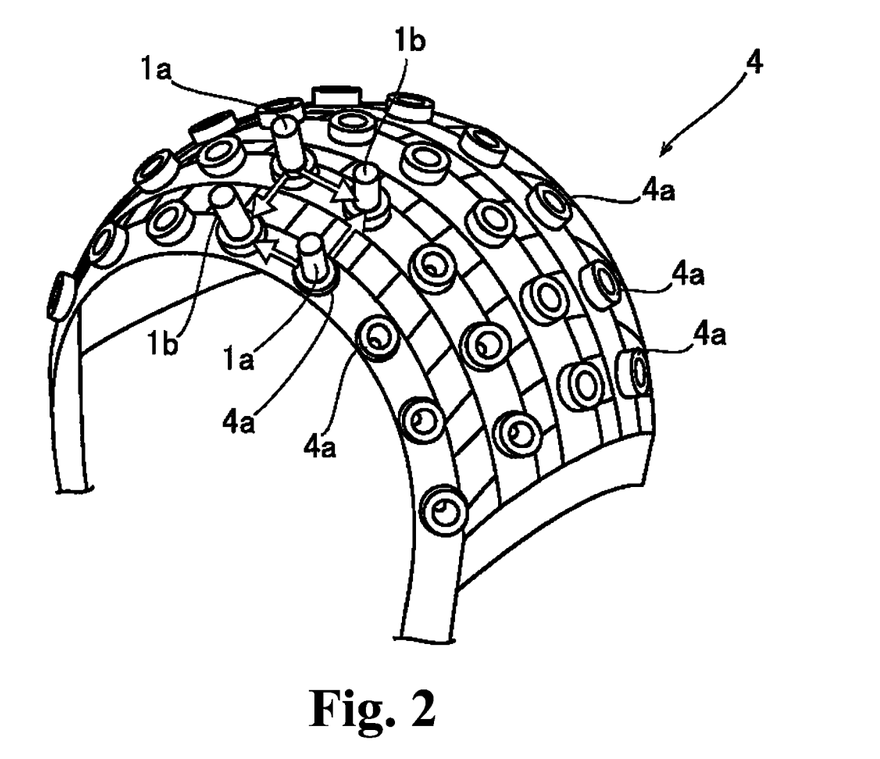
FIG. 2 is a schematic view for explaining a holder used for performing a measurement by an optical measurement apparatus, according to certain embodiments of the present invention.

As shown in FIG. 1, the optical measurement system 100 includes one conveyable type optical measurement apparatus 1 and one portable type optical measurement apparatus 2. These optical measurement apparatus 1 and portable type measurement apparatus 2 each are structured as an independent apparatus capable of separately performing a measuring operation.

Initially, a measurement by the optical measurement apparatus will be briefly explained. The optical measurement apparatus irradiates a measurement light within a wavelength region of a near infrared light from light transmitting probes 1*a* (2*a*) arranged on a head surface of a subject (examinee). The measurement light transmitted (completely transmitted) the subject and/or reflected (reflected in a body) by the subject is detected by making the measurement light incident to the light receiving probes 1*b*(2*b*), to thereby obtain the intensity (light received amount) of the measurement light.

Here, reflecting the brain activity, the amount of hemoglobin in the brain increases, which in turn increases the absorbing amount of the measurement light by the hemoglobin. For this reason, based on the intensity of the obtained measurement light, it becomes possible to acquire the change in the amount of hemoglobin accompanied by the brain activity. The hemoglobin is divided into oxyhemoglobin connected to oxygen and deoxyhemoglobin not connected to oxygen, which are different in light absorption characteristics with each other. For this reason, using measurement lights of a plurality of wavelengths (e.g., three wavelengths of 780 nm, 803 nm, and 830 nm) considering the difference of light absorption characteristics, a measurement is performed. Based on the intensity (light receiving amount) of the obtained measurement light of each wavelength, the calculations of each and a total amount of hemoglobin are performed.

As a result, based on the intensity (light receiving amount) of the measurement light incident to the light receiving probe 1*b*(2*b*), it becomes possible to non-invasively obtain the change in the hemoglobin amount accompanied by the brain activity, i.e., the change in the blood flow rate or the activation state of the oxygen metabolism. The optical measurement apparatus is configured so that a two-dimensional distribution showing how each brain region works can be obtained by measuring at a plurality of points (measurement channels) of a wide area in a brain using the plurality of light transmitting probes 1*a*(2*a*) and the plurality of light receiving probes 1*b*(2*b*).

As shown in FIG. 1, the light transmitting probe 1*a*(2*a*) and the light receiving probe 1*b*(2*b*) each are a cylindrical member to which an optical fiber cable (hereinafter referred to as "optical fiber") 3 is connected, and are structured so that a measurement light can be emitted from or can be made incident to the tip end portion of the cylindrical member. As shown in FIG. 2, the light transmitting probe 1*a*(2*a*) and the light receiving probe 1*b*(2*b*) are attached to a holder 4 for fixing them at predetermined positions on a head surface. The holder 4 is provided with a number of attaching portions 4*a* arranged at equal intervals in a matrix manner. Respective attaching portions 4*a* can mount respective probes in a fixed manner. A user decides the arrangement of probes to the attaching portions 4*a* depending on the region 8 (front of head, top of head, side of head, back of head, etc.) to be measured, and attaches probes to the holder 4. The light transmitting probes 1*a*(2*a*) and the light receiving probes 1*b*(2*b*) are arranged alternately in each of the directions of row and column with respect to each attaching portion 4*a*. With this, a measurement channel (measuring point) is formed between the adjacent light transmitting probe 1*a*(2*a*) and the light receiving probe 1*b*(2*b*).

For example, if two pairs of a total of four pieces of the light transmitting probes 1*a* and the light receiving probes 1*b* are arranged in a rectangular shape, two light receiving probes 1*b* are arranged adjacent to one light transmitting probe 1*a*. Therefore, these two pairs of probes constitute four channels. At this time, the user creates a structural list of the measurement channels and also creates a measurement condition in which light transmitting and light receiving can be performed in an appropriate order by determining the order of lighting of each light transmitting probe 1*a* so that only the measurement light from one light transmitting probe 1*a* is made incident to each light receiving probe 1*b*, and then preforms a measurement.

Next, the apparatus structure of the optical measurement system 100 will be explained.

Figure 3:
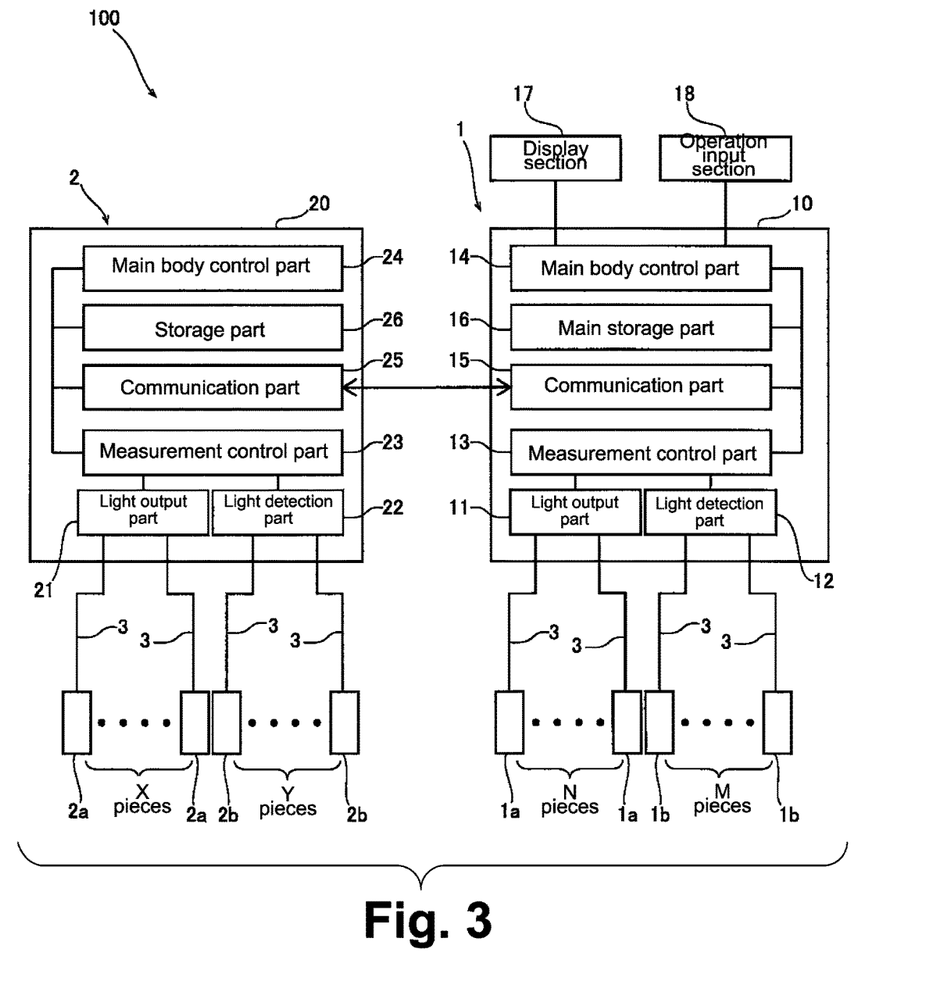
FIG. 3 is a block diagram showing an apparatus structure of an optical measurement system according to certain embodiments of the present invention.

In this embodiment, as shown in FIGS. 1 and 3, the optical measurement apparatus 1 and the optical measurement apparatus 2 are structured in a bidirectional communicable manner by wired or wireless communication. The optical measurement apparatus 1 functions as a master apparatus (main measurement apparatus), and makes the optical measurement apparatus 2 function as a slave apparatus (sub-measurement apparatus) by intercommunication. In one embodiment, the optical measurement apparatus 1 as a master apparatus is configured to not only perform the control of the optical measurement apparatus 1 itself, but also perform the control of the optical measurement apparatus 2 as a slave apparatus, a synchronous measurement, and the storage of the measured data.

Initially, the optical measurement apparatus 1 as a master apparatus will be explained. The optical measurement apparatus 1 is equipped with a box-shaped (carriage-like) main body 10 having wheels 10*a*, and is formed to be larger than the optical measurement apparatus 2 (main body 20). As shown in FIG. 3, the main body 10 accommodates a light output part 11, a light detection part 12, a measurement control part 13, a main body control part 14, a communication part 15, and a main storage part 16. Further, the optical measurement apparatus 1 is provided with a display section 17 arranged on the main body 10 and connected to the main body 10 and an operation input section 18 (see FIG. 1), light transmitting probes 1*a* and light receiving probes 1*b* connected to the main body 10 via optical fibers 3. The optical measurement apparatus 1 can connect a maximum N pieces of light transmitting probes 1*a* and a maximum M pieces of light receiving probes 1*b*, and a total connectable number of probes is N+M pieces. The light transmitting probe 1*a* and the light receiving probe 1*b* are examples of the "second light transmitting terminal" and the "second light receiving terminal" of the present disclosure, respectively. Further, the light output part 11 and the light detection part 12 are examples of the "second light output part, and the "second light detection part" of the present disclosure, respectively. Further, the main body control part 14 is an example of the "second control part" of the present disclosure. The communication part 15 is one example of the "second communication part" of the present disclosure.

The light output part 11 is configured to output a measurement light to the light transmitting probes 1a via optical fibers 3. The light output part 11 is equipped with a semiconductor laser as a light source, and is configured so that measurement lights of a plurality of wavelengths (e.g., three wavelengths of 780 nm, 803 nm, and 830 nm) can be output in a wavelength region of a near infrared light. The light output part 11 can separately or simultaneously output measurement lights to a plurality (maximum N pieces) of connected light transmitting probes 1a.

The light detection part 12 is equipped with a photomultiplier tube as a detector, and is configured to obtain the measurement light incident to the light receiving probe 1b via the optical fiber 3 to detect it. The light detection part 12 is individually capable of detecting the measurement lights from a plurality (maximum M pieces) of connected light receiving probes 1b. When the measurement light emitted from a subject is incident on the light receiving probe 1b, the light detection part 12 detects the incident measurement light and outputs a light receiving amount signal.

The measurement control part 13 performs an operation control of the light output part 11 and the light detection part 12 in accordance with measurement conditions set by the main body control part 14 and/or measurement parameters regarding output intensity of the measurement light and detection sensitivity of the light detection part 12. Further, the measurement control part 13 outputs a drive signal to the output part 11 to thereby control the timing of lighting and extinction of the light output part 11 and also obtain a light receiving mount signal from the light detection part 12.

The main body control part 14 is a computer constituted by CPUs and memories, and is configured to execute various programs stored in the main storage part 16 to perform a measurement operation control of the optical measurement apparatus 1 and to be operated as a main control part (master side control part) for controlling the optical measurement apparatus 2 via the communication part 15. The control of the optical measurement apparatus 2 by the main body control part 14 includes at least a control of the measurement operation by instructing a measurement start, a storage start and a measurement stop of the measured data, and settings of measurement conditions at the time of performing a measurement. Further, in this embodiment, the control of the optical measurement apparatus 2 by the main body control part 14 further includes a synchronous control at the time of a measurement and a control regarding measured data storage and processing of the measured data.

The main body control part 14 controls each of the measurement control part 13, the communication part 15, and the main storage part 16 to thereby perform execution of the measurement operation, calculation of the measured data based on the obtained light receiving amount signal and storage of the measured data to the main storage part 16. Further, the main body control part 14 receives an input operation using the operation input section 18 connected to the main body 10 to perform settings of measurement conditions to the measurement control part 13 and receipt of a measurement start instruction, etc. Further, the main body control part 14 performs various image displays and/or an output of measured data to the display section 17 connected to the main body 10. The operation input section 18 is an input device such as, e.g., a keyboard and a mouse, and the display section 17 is a display device such as, e.g., a liquid-crystal monitor.

The communication part 15 is comprised of a wired or wireless communication module, and is capable of performing data communication between external devices including the optical measurement apparatus 2. The main storage part 16 is comprised of, e.g., an HDD (hard disk drive), and can store various programs to be executed by the main body control part 14 and store measured data obtained by the result of measurements.

The different "parts" described herein may be implemented using different software, firmware, or hardware, or combinations thereof. For example, the control parts, communication parts, and storage parts may be implemented using particular hardware, such as microprocessors, memory chips, various circuit elements, etc., in combination with certain computer programs or other software, and/or firmware. Other "parts" may be implemented with some of the same, and/or different types of hardware, firmware, and/or software.

Next, the optical measurement apparatus 2 as a slave apparatus will be explained. The optical measurement apparatus 2 is equipped with a main body 20 capable of being carried by a subject. The main body 20 accommodates a light output part 21, and a light detection part 22, a measurement control part 23, a main body control part 24, a communication part 25, and a storage part 26. Further, the optical measurement apparatus 2 is equipped with light transmitting probes 2a and light receiving probes 2b connected to the main body 20 via optical fibers 3. The optical measurement apparatus 2 can connect a maximum X pieces of light transmitting probes 2a and a maximum Y pieces of light receiving probes 2b, and a total connectable number of probes is X+Y. The light transmitting probe 2a and the light receiving probe 2b are examples of the "first light transmitting terminal" and the "second light receiving terminal" according to the present disclosure. The light output part 21 and the light detection part 22 are examples of the "first light output part" and the "first light detection part" of the present disclosure. Further, the main body control part 24 is an example of the "first control part" of the present disclosure. Further, the communication part 25 is an example of the "first communication part" of the present disclosure.

The main body 20 of the optical measurement apparatus 2 is formed to be smaller than the main body 10 of the optical measurement apparatus 1 and has a size capable of being worn by a subject. The main body 20 can be carried, and is wearable on a body (for example, a back or a waist of a subject) via an attachment (not illustrated). The connectable number X of the light transmitting probes 2a of the optical measurement apparatus 2 is smaller than the connectable number N of optical measurement apparatus 1, and the connectable number Y of the light receiving probes 2b of the optical measurement apparatus 2 is smaller than the connectable number M of the optical measurement apparatus 1. The total number X+Y of probes connectable to the optical measurement apparatus 2 is smaller than the total number N+M of probes connectable to the optical measurement apparatus 1.

The light output part 21 and the light detection part 22 have basically the same structure as that of the light output part 11 and the light detection part 12 of the optical measurement apparatus 1 except for the connectable number of probes. Further, the measurement control part 23 and the communication part 25 are basically the same as the measurement control part 13 and the communication part 15 of the optical measurement apparatus 1.

The main body control part 24 is a computer constituted by CPUs, memories, etc., and is configured to execute various programs stored in the storage part 26 to perform a measurement operation control of the optical measurement apparatus 2 and to be operated as a sub control part (slave side control part) for controlling the optical measurement apparatus 2 in accordance with a control instruction from the main body control part 14 sent via the communication part 15. With this, the optical measurement apparatus 2 operates as a slave apparatus to the optical measurement apparatus 1.

The main body control part 24 controls each of the measurement control part 23, the communication part 25, and the storage part 26, and performs settings of various parameters regarding the measurement conditions or measurement, execution of the measurement operation, calculation of the measured data based on the obtained light receiving amount signal in accordance with the control by the optical measurement apparatus 1 (main body control part 14).

In certain embodiments, the storage part 26 is comprised of, e.g., a nonvolatile memory, etc., and stores various programs to be executed by the main body control part 24 and temporarily stores measured data obtained by the result of measurements. Measured data are temporarily stored in the storage part 26 and then transmitted to the optical measurement apparatus 1 or an external computer (not illustrated) for executing data processing, etc., via the communication part 25. In the portable type optical measurement apparatus 2, the operation input section 18 and the display section 17 are not connected. For this reason, settings of measurement conditions for the optical measurement apparatus 2 is performed by a user using the operation input section 18 and the display section 17 of the operation measurement apparatus 1 or an external computer.

As explained above, the optical measurement system 100 according to this embodiment is structured. In this embodiment, other than using the optical measurement apparatuses 1 and 2 as an independent apparatus, the optical measurement system 100 is structured so that operations can be performed by the intercommunication of the optical measurement apparatus 1 as a master apparatus and the optical measurement apparatus 2 as a slave apparatus in the following three operation forms. Hereinafter, with reference to FIGS. 1, 3 and 4, the three operation forms will be explained together with the schematic operation of the optical measurement system 100.

The first operation form is, as shown in FIG. 1, a form in which both the optical measurement apparatuses 1 and 2 are used to perform measurements by the optical measurement apparatuses 1 and 2 with respect to separate subjects in synchronization. In this case, for example, for one subject, by the optical measurement apparatus 1, a measurement is performed using N or fewer light transmitting probes 1a and M or fewer light receiving probes 1b. On the other hand, for the other subject, by the optical measurement apparatus 2, a measurement is performed using X or fewer transmitting probes 2a and Y or fewer light receiving probes 2b.

Figure 4:
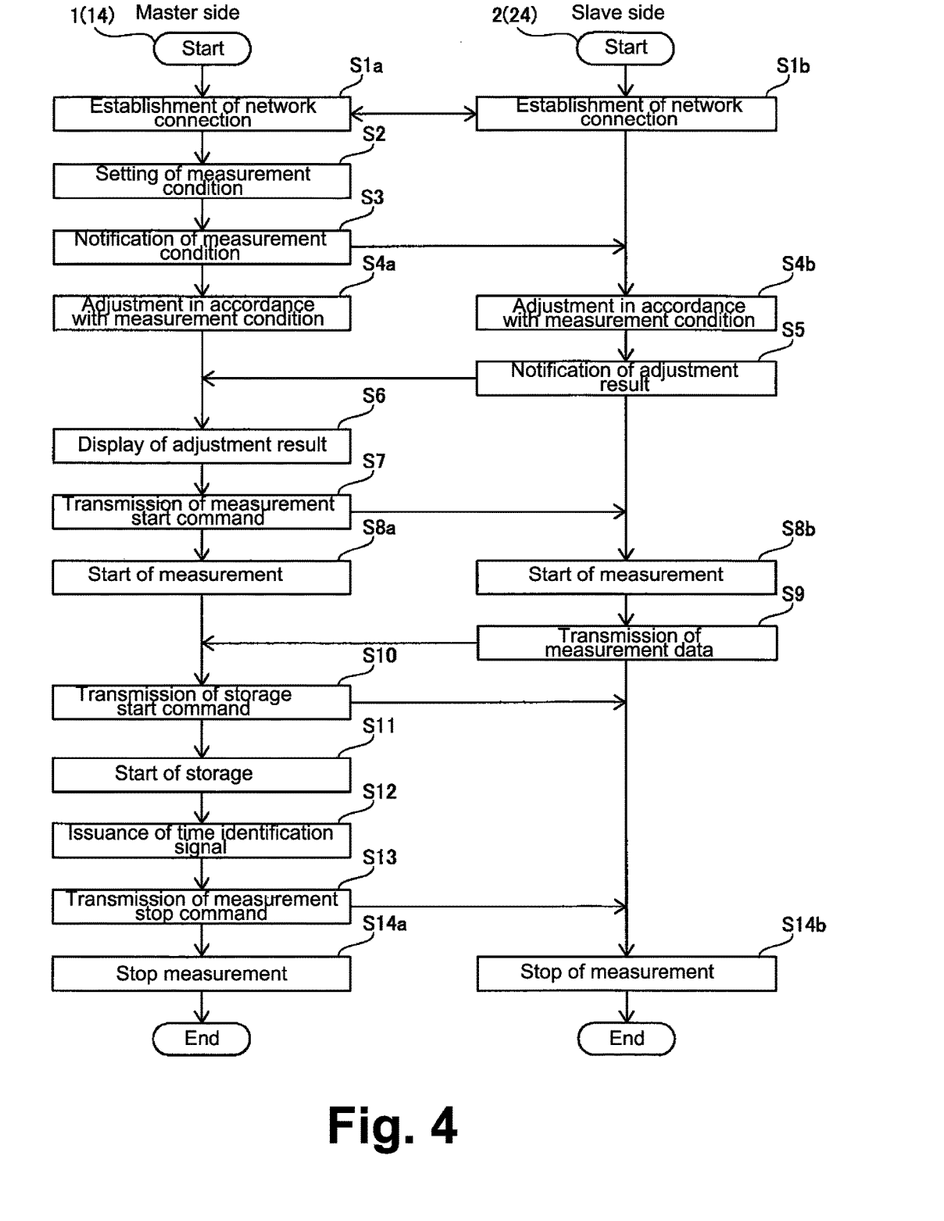
FIG. 4 is a flowchart schematically showing an operation of an optical measurement system according to one embodiment of the present invention.

As shown in FIGS. 3 and 4, first, in Step S1a and S1b, the main body control part 14 of the optical measurement apparatus 1 establishes a network connection between the communication part 15 and the communication part 25 of the optical measurement apparatus 2. With this, it becomes possible to perform a bidirectional communication between the optical measurement apparatus 1 and the optical measurement apparatus 2. The communication uses, for example, a TCP/IP protocol.

After establishment of the network connection, in Step S2, the main body control part 14 of the optical measurement apparatus 1 performs settings of measurement conditions based on the input operation of a user used the operation input section 18 and the display section 17. With this, various measurement conditions such as the arrangement condition (structural list of measurement channels) of the light transmitting probes 1a and the light receiving probes 1b with respect to a subject, the order of lighting based on the arrangement conditions, the number of repetition times, the timing between the lighting and the light detection, etc. The main body control part 14 sets the measurement conditions by transmitting them to the measurement control part 13.

At this time, the user also inputs the measurement conditions of the subject to be measured by the optical measurement apparatus 2 using the operation input section 18 and the display section 17 of the optical measurement apparatus 1. For example, the main body control part 14 may create measurement conditions of the optical measurement apparatus 2, such as, e.g., the arrangement conditions (structural list of measurement channels) of the light transmitting probes 2a and the light receiving probes 2b, the order of lighting based on the arrangement conditions, the number of repetition times, the timing between the lighting and the light detection. Since the subjects are different, the measurement conditions for the optical measurement apparatus 2 and the measurement conditions for the optical measurement apparatus 1 are created separately and independently.

Subsequently, in Step S3, the main body control part 14 of the optical measurement apparatus 1 notifies the optical measurement apparatus 2 side of the measurement conditions of the optical measurement apparatus 2 via the communication part 15. The main body control part 24 of the optical measurement apparatus 1 that received the measurement conditions sets measurement conditions to the measurement control part 23.

In Step S4a, the main body control part 14 of the optical measurement apparatus 1 issues an adjustment instruction such as the output intensity or the detection sensitivity (amplification factor of an optical signal) depending on the measurement conditions to the measurement control part 13 to perform adjustment of the light output part 11 and the light detection part 12. In the same manner, in Step S4b, the main body control part 24 of the optical measurement apparatus 2 issue an adjustment instruction to the measurement control part 23 to perform adjustments of the light output part 21 and the light detection part 22.

In Step S5, the adjustment results are notified from the main body control part 24 (communication part 25) of the optical measurement apparatus 2 to the optical measurement apparatus 1 side. In Step S6, the main body control part 14 of the optical measurement apparatus 1 receives the notification of adjustment results and makes the display section 17 display the notification together with the adjustment results of the optical measurement apparatus 1. With this, the measurement preparation becomes ready, and the main body control part 14 of the optical measurement apparatus 1 waits for an input of a measurement start instruction by the user.

When the main body control part 14 of the optical measurement apparatus 1 receives the measurement start input using the operation input section 18, the routine proceeds to Step S7, and the main body control part 14 transmits a measurement start command to the optical measurement apparatus 2. Then, in Step S8a and Step S8b, the main body control part 14 of the optical measurement apparatus 1 and the main body control part 24 of the optical measurement apparatus 2 start measurements in synchronization.

The measured data after the measurement start are received by the main body control part 14 of the optical measurement apparatus 1 and the main body control part 24 of the optical measurement apparatus 2, respectively. In Step S9, the main body control part 24 performs prescribed data processing to the measured data and then transmits the measurement data to the optical measurement apparatus 1 via the communication part 25. In the optical measurement apparatus 1, the main body control part 14 makes the display section 17 display the received measured data of the optical measurement apparatus 2 together with the measured data of the optical measurement apparatus 1 itself.

Next, when the main body control part 14 of the optical measurement apparatus 1 receives the storage start input by a user using the operation input section 18, in Step 10, the main body control part 14 transmits the storage start command to the optical measurement apparatus 2. Then, the routine proceeds to Step S11, and the main body control part 14 stores the measured data of itself and the received measured data of the optical measurement apparatus 2 in the main storage part 16 of the optical measurement apparatus 1. At this time, the measured data of the optical measurement apparatus 1 and the measured data of the optical measurement apparatus 2 are separately stored as independent data files.

In the brain function measurement by the optical measurement apparatus, a method of comparing hemoglobin variations between the task and the rest in which an acting stage (task) and a resting stage (rest) are repeated or a method of comparing hemoglobin variations between a certain period before a certain event occurs and a certain period after an event occurs are used, and it may be required to administrate the time used to switch between a task and a rest and/or the time when an event occurred. For this reason, after the start of storage, in Step S12, based on the input operation using the operation input section 18, the main body control part 14 issues a time identification signal such as, e.g., an event signal or a mark signal, adds the time identification signal to the measured data at the time when the input was received and stores it to the main storage part 16.

Further, when the main body control part 14 of the optical measurement apparatus 1 receives a measurement stop input by the user using the operation input section 18, the routine proceeds Step S13, and the main body control part 14 transmits a measurement start command to the optical measurement apparatus 2. The main body control part 14 transmits the measurement stop command to the optical measurement apparatus 2. Then, in Steps S14*a* and Step S14*b*, the main body control part 14 of the optical measurement apparatus 2 and the main body control part 24 of the optical measurement apparatus 2 stop measurements.

With this, the synchronous measurements (first operation form) by the optical measurement apparatus 1 and the optical measurement apparatus 2 to separate subjects are performed.

The second operation form is a form in which the optical measurement apparatuses 1 and 2 are used together and the optical measurement apparatuses 1 and 2 perform measurements with respect to the same subject in synchronization. In this case, the measurement is performed using the N+X or fewer light transmitting probes 1*a*(2*a*) and M+Y or fewer light receiving probes 1*b*(2*b*).

In this case, in Step S2 in FIG. 4, integrated measurement conditions integrated for the optical measurement apparatus 1 and the optical measurement apparatus 2 are set. That is, based on the arrangement of the light transmitting probes 1*a* and the light receiving probes 1*b* on the optical measurement apparatus 1 side for the same subject and the light transmitting probes 2*a* and the light receiving probes 2*b* on the optical measurement apparatus 2 side, measurement conditions are created. In this case, it is not required to create measurement conditions separately for each apparatus, and is possible to create measurement conditions uniformly utilizing the operation input section 18 and the display section 17 of the optical measurement apparatus 1.

When measurement conditions are set, in Step S3, the main body control part 14 of the optical measurement apparatus 1 notifies the optical measurement apparatus 2 of the measurement conditions while separating the measurement conditions in charge of the optical measurement apparatus 2 (light transmitting probe 2*a* and light transmitting probe 2*b*). The measurement conditions in charge (light transmitting probe 1*a* and light receiving probe 1*b*) of the optical measurement apparatus 1 are set in the measurement control part 13 of the optical measurement apparatus 1 itself.

Further, in Step S11, the main body control part 14 of the optical measurement apparatus 1 consolidates its own measured data and received measured data of the measurement apparatus 2 and stores them in the main storage part 16 of the optical measurement apparatus 1 as a single data file. For this reason, without requiring operations for data replacement and/or data consolidation, it becomes possible to integrally perform addition of a time identification signal in Step S12, data processing after measurements, or analysis operations.

Processing in another step in the second operation form is the same as that in the first operation form, and therefore the explanation will be omitted.

Next, the third operation form is a form in which in a single use of the optical measurement apparatus 2, the measured operation control, data storage and the data display from the optical measurement apparatus 1 side are executed. In this case, a measurement is performed by the optical measurement apparatus 2 using X or fewer light transmitting probes 2*a* and Y or fewer light transmitting probes 2*b* for a subject.

In this case, in Step S2 in FIG. 4, a user independently sets measurement conditions only to the optical measurement apparatus 2 utilizing the display section 17 and the operation input section 18. That is, the main body control part 14 creates measurement conditions of the optical measurement apparatus 2 based on the input operation by the user.

When measurement conditions are set, in Step S3, the main body control part 14 of the optical measurement apparatus 1 notifies the optical measurement apparatus 2 of the set measurement conditions for the optical measurement apparatus 2. In this case, no measurement is performed on the optical measurement apparatus 1 side, and therefore no measurement condition is set to the optical measurement apparatus 1 itself.

Further, in Step S11, the main body control part 14 of the optical measurement apparatus 1 stores the received measured data of the measurement apparatus 2 in the main storage part 16 of the optical measurement apparatus 1 as an independent data file. For this reason, a display of the stored measured data, data processing after measurements, an analysis operation, etc., can be performed by the operation input section 18 of the optical measurement apparatus 1 and the display section 17 without using an external computer.

Processing in another step in the third operation form may be the same as that in the first operation form, and therefore the explanation will be omitted.

As explained above, in the aforementioned first to third operation forms, the optical measurement apparatus 1 as a master apparatus not only performs its control but also performs a measurement control of the optical measurement apparatus 2 as a slave apparatus, performs settings of various parameters regarding measurement conditions of the slave apparatus and measurements by operation inputs using the operation input section 18, and performs synchronization at the time of measurements. Further, the optical measurement apparatus 1 receives measured data of the optical measurement apparatus 2 as a slave apparatus and stores the data in the main storage part 16, and the optical measurement apparatus 1 administers the measured data obtained by the optical measurement apparatus 1 and the measured data of the optical measurement apparatus 2 separately or integrally. As a result, in this embodiment, the optical measurement apparatus 1 high in restrictive to a subject is complimented by the portable type optical measurement apparatus 2, and the optical measurement apparatus 2 which requires an external computer is complimented by the optical measurement apparatus 1. Thus, variety of operations can be performed. Further, in this case, although the main body control part 14 of the master apparatus is required to have a larger processing ability than the main body control part 24 of the slave apparatus, by using the conveyable type optical measurement apparatus 1 having less size limitation as a master apparatus, it becomes easily possible to structure an optical measurement system 100.

In this embodiment, as explained above, it is structured such that the optical measurement apparatus 1 can be communicated with the optical measurement apparatus 2, and measurement settings and measurement controls are executed based on input operations from the operation input section 18. Further, it is configured such that the optical measurement apparatus 1 operates as a main measurement apparatus (master apparatus) for executing measurement condition settings and measurement controls of the optical measurement apparatus 2 by communication. It is further configured such that the optical measurement apparatus 2 operates as a sub-measurement apparatus (slave apparatus) for executing measurement condition settings and measurement controls in accordance with the control by the optical measurement apparatus 1. With this, it becomes possible to perform measurement condition settings and measurement controls of the optical measurement apparatus 2 on the optical measurement apparatus 1 side.

Accordingly, if there are the optical measurement apparatus 1 and the optical measurement apparatus 2, it becomes possible not only to use respective apparatuses depending on an intended purpose, but also to increase the measurement channel number by operating the optical measurement apparatus 2 and the optical measurement apparatus 1 together and perform measurements of a plurality of subjects by the optical measurement apparatus 2 and the optical measurement apparatus 1, respectively. Further, since measurement condition settings and measurement controls of the optical measurement apparatus 2 can be performed using the operation input section 18 of the optical measurement apparatus 1, it is not required to prepare an external computer which was conventionally required for a portable type apparatus. As a result, in the case of utilizing both types of optical measurement apparatuses, i.e., a portable type (mobile type) optical measurement apparatus 2 and a conveyable type (non-portable type) optical measurement apparatus, it becomes possible to obtain an optical measurement system capable of being utilized for various purposes or in various usage environments while restraining additional capital investments.

Further, in this embodiment, as explained above, the optical measurement apparatus 2 is configured to be controllable so that the optical measurement apparatus 1 executes the measurement operation of the optical measurement apparatus 1 and the measurement operation of the optical measurement apparatus 2 in synchronization. With this, for example, by using both the optical measurement apparatus 1 and the optical measurement apparatus 2 together, synchronous measurements for one or a plurality of subjects can be performed simultaneously.

Further, in this embodiment, as explained above, the optical measurement apparatus 1 is configured to be able to obtain measured data of the optical measurement apparatus 2 by communication and store the obtained measured data in the main storage part 16. With this, since the measured data obtained by the optical measurement apparatus 2 can be administered on the optical measurement apparatus 1 side, it is not required to prepare an external computer for the measured data administration and additional capital investment can be restrained. Further, in the case of operating the optical measurement apparatus 1 and the optical measurement apparatus 2 together, measured data comparison and/or integration can be easily performed without requiring any measured data transferring operations between the apparatuses.

Further, in this embodiment, as explained above, in cases where the optical measurement apparatus 1 and the optical measurement apparatus 2 respectively perform measurement operations for a plurality of subjects (first operation form), the optical measurement apparatus 1 is configured such that the measurement operation of the optical measurement apparatus 1 for one subject and the measurement operation of the optical measurement apparatus 2 for another subject are synchronized and the measured data of the optical measurement apparatus 1 and the measured data of the optical measurement apparatus 2 are stored in the main storage part 16 separately. With this, without preparing a plurality of same type apparatuses, a plurality of subjects can be measured in synchronization. Also in this case, without requiring measured data transferring operations between apparatuses, a comparison between data, etc., can be performed only by the optical measurement apparatus 1.

Further, in this embodiment, as explained above, in cases where the optical measurement apparatus 1 and the optical measurement apparatus 2 perform a measurement operation for the same subject (second operation form), the optical measurement apparatus 1 is configured such that the measurement operation of the optical measurement apparatus 1 and the measurement operation of the optical measurement apparatus 2 are synchronized and the measured data of the optical measurement apparatus 1 and the measured data of the optical measurement apparatus 2 are stored in the main storage part 16 integrally. By structuring as mentioned above, only by the existing apparatuses (the optical measurement apparatus 1 and the optical measurement apparatus 2), a measurement can be performed by increasing the measurement channel number. Also in this case, without requiring measured data transferring operations between apparatuses, the measured data of each apparatus can be administered as single measured data on the optical measurement apparatus 1 side.

Further, in this embodiment, as explained above, in cases where a measurement for a subject is performed only by the optical measurement apparatus 2 (third operation form), the optical measurement apparatus 1 is configured such that the measurement operation of the optical measurement apparatus 2 is controlled, the measured data of the optical measurement apparatus 2 is obtained and stored in the main storage part 16 independently of the measured data of the optical measurement apparatus 1. With this, even in the case of using the optical measurement apparatus 2 alone, any external computer can be eliminated. For this reason, while restraining additional capital investments, various applications can be dealt only by the existing optical measurement apparatus 1 and the optical measurement apparatus 2.

Further, in this embodiment, as explained above, the optical measurement apparatus 2 is equipped with the light output part 21, the light detection part 22, the communication part 25, and the main body control part 24, while the optical measurement apparatus 1 is equipped with the light output part 11, the light detection part 12, the communication part 15, a main body control part 14, a display section 17 and the operation input section 18. With this, it becomes possible to structure the optical measurement apparatus 2 and the optical measurement apparatus 1 independently measurable and communicable each other. By providing the display section 17 and the operation input section 18 to the optical measurement apparatus 1, without preparing an external display device, etc., the measurement condition settings of the optical measurement apparatus 2 and operations for measurements can be performed only by the optical measurement apparatus 1.

The disclosed embodiments should be considered to be illustrative in all aspects and non-limitation. The scope of the present invention should be determined in view of the claims, and includes the meaning equivalent to claims and all modifications within their scope, and should not be limited by the various examples discussed herein.

For example, in the aforementioned embodiments, an explanation was directed to the example applied to an optical measurement system constituted by a single conveyable type optical measurement apparatus 1 (master apparatus) and a single portable type optical measurement apparatus 2 (slave apparatus), but the present invention is not limited to it. The present embodiments can be applied to an optical measurement system having a plurality of optical measurement apparatuses as slave apparatuses.

Further, in the aforementioned embodiments, an explanation was directed to the example in which the optical measurement apparatus 1 (master apparatus) performs the measurement condition settings and controls of the optical measurement apparatus 2 (slave apparatus), synchronization at the time of measurement and storage of measured data, but the present invention is not limited to it. For example, in certain embodiments, at least the optical measurement apparatus 1 (master apparatus) performs the measurement condition settings and controls of the optical measurement apparatus 2 (slave apparatus). As for the synchronization and storage of measured data, it can be configured to use a separate means for performing synchronous measurements or store the measured data for each separate apparatus.

Further, in the aforementioned embodiments, the explanation was directed to the example in which a carriage-like conveyable type optical measurement apparatus 1 (master apparatus) is provided, but the present invention is not limited to it. For example, the optical measurement apparatus 1 (master apparatus) can be a stationary apparatus (non-portable type measurement apparatus) to be fixedly arranged.

Further, in the aforementioned embodiments, an explanation was directed to the example in which the optical measurement apparatus 2 (slave apparatus) capable of being mounted on a subject is provided, but the present invention is not limited to it. For example, the optical measurement apparatus 2 (slave apparatus) can be an optical measurement apparatus that a subject can carry with hand or over the shoulder.

Further, in the aforementioned embodiments, an explanation was directed to the example in which the optical measurement apparatus 1 (master apparatus) is provided with a display section, but the present invention is not limited to it. For example, in place of providing a display section on the optical measurement apparatus 1 (master apparatus), it can be configured such that the optical measurement apparatus 1 (master apparatus) can be connected to an external display device to display measured data, etc., on the external display device.

Further, in the aforementioned embodiments, an explanation was directed to the example in which the optical measurement apparatus measures hemoglobin amount variations in a brain of a subject, but the present invention is not limited to it. In addition to the hemoglobin amount variations in a brain, it can be configured to measure data of a part of a body (for example, fingers) of a subject.

The entire disclosure of Japanese Patent Application No. 2012-277462 filed on Dec. 19, 2012, which describes certain features related to the present disclosure, is incorporated herein by reference in its entirety.

The terms and descriptions used herein are used only for explanatory purposes and the present invention is not limited to them. While various aspects of the present invention may be embodied in many different forms, a number of illustrative embodiments are described herein with the understanding that the present disclosure is to be considered as providing examples of the principles of the invention and such examples are not intended to limit the invention to the specific embodiments described herein and/or illustrated herein.

The claims are to be interpreted broadly based on the language employed in the claims and not limited to examples described in the present specification or during the prosecution of the application, which examples are to be construed as non-exclusive.

The present invention is not limited to the various embodiments described herein, but includes any and all embodiments having equivalent elements, modifications, omissions, combinations (e.g., of aspects across various embodiments), adaptations and/or alterations as would be appreciated by those in the art based on the present disclosure.

In this disclosure and during the prosecution of this application, the terminology "present invention" or "invention" is meant as a non-specific, general reference and may be used as a reference to one or more aspects within the present disclosure. The language present invention or invention should not be improperly interpreted as an identification of criticality, should not be improperly interpreted as applying across all aspects or embodiments (i.e., it should be understood that the present invention has a number of aspects and embodiments), and should not be improperly interpreted as limiting the scope of the application or claims. In this disclosure and during the prosecution of this application, the terminology "embodiment" can be used to describe any aspect, feature, process or step, any combination thereof, and/or any portion thereof, etc. In some examples, various embodiments may include overlapping features.

What is claimed is:

1. An optical measurement system comprising:
 a portable type measurement apparatus configured to measure a subject by irradiating a measurement light from a first light transmitting terminal to the subject and receiving the measurement light emitted outside from the subject by a first light receiving terminal; and a non-portable type measurement apparatus larger than the portable type measurement apparatus, the non-portable type measurement apparatus being configured to measure the subject independently of the portable type measurement apparatus by irradiating a measurement light from a second light transmitting terminal to the subject and receiving the measurement light emitted outside from the subject by a second light receiving terminal, wherein the non-portable type measurement apparatus is configured to be communicable to the portable type measurement apparatus and to be operated as a main measurement apparatus which executes measurement condition settings and measurement controls based on an input operation from an operation input section and also executes measurement condition settings and measurement controls of the portable type measurement apparatus by communication, wherein the portable type measurement apparatus is configured to measure the subject independently of the non-portable type measurement apparatus and to be operated as a sub-measurement apparatus which executes measurement condition settings and measurement controls based on a control of the non-portable type measurement apparatus, wherein the non-portable type measurement apparatus further includes a main storage part for storing measured data, and is configured to obtain measured data of the portable type measurement apparatus by communication and store the obtained measured data in the main storage part, wherein in cases where the non-portable type measurement apparatus and the portable type measurement apparatus perform measurement operations for the same subject, the non-portable type measurement apparatus is configured such that the measurement operation of the non-portable type measurement apparatus and the measurement operation of the portable type measurement apparatus are synchronized and the measured data of the non-portable type measurement apparatus and the measured data of the portable type measurement apparatus are integrally stored in the main storage part, and wherein the non-portable type measurement apparatus is configured to control the portable type measurement apparatus so as to simultaneously execute the measurement operation of the non-portable type measurement apparatus and the measurement operation of the portable type measurement apparatus in synchronization.

2. The optical measurement system as recited in claim 1, wherein the portable type measurement apparatus includes a first light output part for outputting the measurement light to the first light transmitting terminal, a first light detection part for detecting the measurement light received from the first light receiving terminal, a first communication part, and a first measurement control circuit for performing a measurement operation control, and wherein the non-portable type measurement apparatus includes a second light output part for outputting the measurement light to the second light transmitting terminal, a second light detection part for detecting the measurement light received from the second light receiving terminal, a second communication part communicable to the first communication part of the portable type measurement apparatus, a second measurement control circuit performing a measurement operation control, a display section, and the operation input section.

3. An optical measurement system comprising:

a portable type measurement apparatus including a first light output part for outputting a measurement light to a first light transmitting terminal, a first light detection part for detecting the measurement light received from a first light receiving terminal, a first communication part, and a first measurement control circuit for performing a measurement operation control; and a non-portable type measurement apparatus larger than the portable type measurement apparatus, including a second light output part for outputting the measurement light to a second light transmitting terminal, a second light detection part for detecting the measurement light received from a second light receiving terminal, a second communication part communicable to the first communication part of the portable type measurement apparatus, a second measurement control circuit for performing a measurement operation control, and an operation input section for receiving an input operation, wherein the portable type measurement apparatus and the non-portable type measurement apparatus are configured to independently measure a subject by receiving the measurement light irradiated from the first light transmitting terminal and the second light transmitting terminal to the subject and emitted outside from the subject, wherein the second measurement control circuit of the non-portable type measurement apparatus is configured to be operated as a main measurement apparatus which executes measurement condition settings and measurement controls of the non-portable type measurement apparatus based on an input operation from the operation input section and also executes measurement condition settings and measurement controls of the portable type measurement apparatus by communication, wherein the first measurement control circuit of the portable type measurement apparatus is configured to be operated as a sub-measurement apparatus which executes measurement condition settings and measurement controls of the portable type measurement apparatus based on a control by the second measurement control circuit, wherein the non-portable type measurement apparatus further includes a main storage part for storing measured data, and is configured to obtain measured data of the portable type measurement apparatus by communication and store the obtained measured data in the main storage part, wherein in cases where the non-portable type measurement apparatus and the portable type measurement apparatus perform measurement operations for the same subject, the non-portable type measurement apparatus is configured such that the measurement operation of the non-portable type measurement apparatus and the measurement operation of the portable type measurement apparatus are synchronized and the measured data of the non-portable type measurement apparatus and the measured data of the portable type measurement apparatus are integrally stored in the main storage part, and wherein the non-portable type measurement apparatus is configured to control the portable type measurement apparatus so as to simultaneously execute the measurement operation of the non-portable type measurement apparatus and the measurement operation of the portable type measurement apparatus in synchronization.

4. An optical measurement apparatus formed to be larger than a portable type measurement apparatus, the portable type measurement apparatus including a first light output part for outputting a measurement light to a first light transmitting terminal, a first light detection part for detecting the measurement light received from a first light receiving terminal, a first communication part, and a first measurement control circuit for performing a measurement operation control, the portable type measurement apparatus being configured to perform a measurement operation of a subject by receiving the measurement light emitted outside from the subject, the optical measurement apparatus comprising:
a second light output part configured to output the measurement light to a second light transmitting terminal;
a second light detection part configured to detect the measurement light received from a second light receiving terminal;
a second communication part communicable to the first communication part of the portable type measurement apparatus;
a second measurement control circuit configured to perform a measurement operation control; and
an operation input section configured to receive an input operation,
wherein the optical measurement apparatus is configured to perform a measurement operation of the subject independently of the portable type measurement apparatus by receiving the measurement light irradiated from the second light transmitting terminal to the subject and emitted outside from the subject,
wherein the second measurement control circuit is configured to make the first measurement control circuit of the portable type measurement apparatus operate as a sub control part for executing measurement condition settings and measurement controls of the portable type measurement apparatus in accordance with a control by operating as a main control part for executing the measurement condition settings and the measurement controls based on an input operation of the operation input section and executing the measurement condition settings and the measurement controls of the portable type measurement apparatus by communication,
wherein the optical measurement apparatus further includes a main storage part for storing measured data, and is configured to obtain measured data of the portable type measurement apparatus by communication and store the obtained measured data in the main storage part,
wherein in cases where the optical measurement apparatus and the portable type measurement apparatus perform measurement operations for the same subject, the optical measurement apparatus is configured such that the measurement operation of the optical measurement apparatus and the measurement operation of the portable type measurement apparatus are synchronized and the measured data of the optical measurement apparatus and the measured data of the portable type measurement apparatus are integrally stored in the main storage part, and
wherein the optical measurement apparatus is configured to control the portable type measurement apparatus so as to simultaneously execute the measurement operation of the optical measurement apparatus and the measurement operation of the portable type measurement apparatus in synchronization.

5. The optical measurement system according to claim 3, wherein the non-portable type measurement apparatus includes a display section.

6. The optical measurement apparatus according to claim 4, wherein the optical measurement apparatus includes a display section.

7. An optical measurement method that uses a portable type measurement apparatus and a non-portable type measurement apparatus larger than the portable type measurement apparatus, wherein the portable type measurement apparatus includes a first light output part for outputting a measurement light to a first light transmitting terminal, a first light detection part for detecting the measurement light received from a first light receiving terminal, a first communication part, and a first measurement control circuit for performing a measurement operation control, and the non-portable type measurement apparatus includes a second light output part for outputting the measurement light to a second light transmitting terminal, a second light detection part for detecting the measurement light received from a second light receiving terminal, a second communication part communicable to the first communication part of the portable type measurement apparatus, a second measurement control circuit for performing a measurement operation control, and an operation input section for receiving an input operation, the method comprising:

independently measuring a subject by receiving the measurement light irradiated from the first light transmitting terminal and the second light transmitting terminal to the subject and emitted outside from the subject;
executing, by utilizing the second measurement control circuit of the non-portable type measurement apparatus, measurement condition settings and measurement controls of the non-portable type measurement apparatus based on an input operation from the operation input section and measurement condition settings and measurement controls of the portable type measurement apparatus by communication;
executing, by utilizing the first measurement control circuit of the portable type measurement apparatus, measurement condition settings and measurement controls of the portable type measurement apparatus based on a control by the second measurement control circuit;
obtaining, by utilizing the non-portable type measurement apparatus, measured data of the portable type measurement apparatus by communication; and
storing the obtained measured data in a main storage part included in the non-portable type measurement apparatus, and
wherein in cases where the non-portable type measurement apparatus and the portable type measurement apparatus perform measurement operations for the same subject, the method further comprising:
synchronizing the measurement operation of the non-portable type measurement apparatus and the measurement operation of the portable type measurement apparatus;
simultaneously executing the measurement operation of the non-portable type measurement apparatus and the measurement operation of the portable type measurement apparatus in synchronization; and
integrally storing the measured data of the non-portable type measurement apparatus and the measured data of the portable type measurement apparatus in the main storage part.

8. The method according to claim 7, wherein the non-portable type measurement apparatus includes a display section.

\* \* \* \* \*